United States Patent [19]

Ertel et al.

[11] 4,061,767

[45] Dec. 6, 1977

[54] CYANO ACETIC ACID ANILIDE DERIVATIVES, PROCESS FOR THEIR MANUFACTURE AND COMPOSITIONS CONTAINING THESE COMPOUNDS

[75] Inventors: Hartmut Ertel; Günther Heubach, both of Kelkheim, Taunus; Erhard Wolf, Hofheim, Taunus, all of Germany

[73] Assignee: Hoechst Aktiengesellschaft, Frankfurt am Main, Germany

[21] Appl. No.: 692,318

[22] Filed: June 3, 1976

[30] Foreign Application Priority Data

June 5, 1975   Germany ............................. 2524929

[51] Int. Cl.$^2$ ................... A61K 31/36; A61K 31/275; C07C 121/78; C07D 17/06
[52] U.S. Cl. ............................... 424/282; 260/307 H; 260/340.5 R; 260/465 D; 260/562 K; 424/304
[58] Field of Search ....... 260/465 D, 307 H, 340.5 R; 424/304, 282

[56] References Cited

U.S. PATENT DOCUMENTS

| 2,288,863 | 7/1942 | Wenner | 260/307 H |
| 2,721,799 | 10/1955 | Edwards et al. | 260/465 X |

OTHER PUBLICATIONS

Dains et al., J. Am. Chem. Soc., vol. 35, pp. 965–969 relied on (1913).

*Primary Examiner*—Dolph H. Torrence
*Attorney, Agent, or Firm*—Curtis, Morris & Safford

[57] ABSTRACT

A 2-hydroxyethylidene-cyano acetic acid anilide is prepared by heating an acetoacetic acid anilide with an orthoformic acid ester and acetic anhydride, isolating the resulting 2-alkoxymethylene-acetoacetic acid anilide and treating it with hydroxylamine and the isoxazole so obtained with a base, and optionally reacting the resulting alkali metal or ammonium salt with a mineral acid or a strong organic acid. The compounds of the invention have anti-inflammatory and analgesic activity.

8 Claims, No Drawings

CYANO ACETIC ACID ANILIDE DERIVATIVES, PROCESS FOR THEIR MANUFACTURE AND COMPOSITIONS CONTAINING THESE COMPOUNDS

The present invention relates to new 2-hydroxyethylidene-cyano acetic acid anilides of the formula I

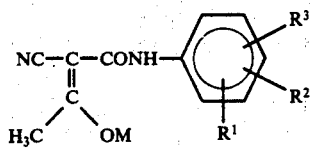

in which $R^1$, $R^2$ and $R_3$, which may be identical or different, each stands for an alkyl group of 1, 2 or 3 carbon atoms, an alkoxy group of 1, 2 or 3 carbon atoms, an alkylthio group of 1, 2 or 3 carbon atoms, which groups may be substituted entirely or partly by identical or different halogen atoms, such as fluorine, chlorine, bromine or iodine; for a halogen atom, such as a fluorine, chlorine, bromine or iodine atom; for a nitro, cyano or alkoxycarbonyl group of 1, 2 or 3 carbon atoms in the alkyl moiety; $R^1$ and $R^2$ each further stands for hydrogen, in which case, however, $R^3$ cannot stand for methyl but additionally stands for a phenyl group which may carry one or two fluorine, chlorine, bromine or iodine atoms, alkyl groups of 1, 2 or 3 carbon atoms or alkoxy groups of 1, 2 or 3 carbon atoms, or for a phenoxy group which may carry one or two fluorine, chlorine, bromine or iodine atoms, alkyl groups of 1, 2, or 3 carbon atoms or alkoxy groups of 1, 2 or 3 carbon atoms, or $R^1$ stands for hydrogen, and $R^2$ and $R^3$ together stand for a methylene-dioxy group, or together with the phenyl ring, to which they are linked, they stand for a naphthalene ring, and in which M stands for hydrogen, an alkali metal, such as sodium or potassium, or ammonium.

Preferred are compounds of formula I, in which $R^1$ and $R^2$ each stands for hydrogen, $R^3$ stands for a halogen atom, such as a fluorine, chlorine or bromine atoms, the $CF_3$-group or an alkoxy group of 1 or 2 carbon atoms which may be substituted entirely or partly by identical or different halogen atoms, especially fluorine or chlorine atoms.

Furthermore preferred are compounds of formula I, in which $R^1$ stands for hydrogen, and $R^2$ and $R^3$, which may be identical or different, each stands for a halogen atom, such as a fluorine, chlorine or bromine atom, or the $CF_3$-group.

Still further preferred are compounds of formula I, in which $R^1$ stands for hydrogen, $R^2$ for an alkyl group of 1 or 2 carbon atoms, and $R^3$ for a halogen atom, such as a fluorine, chlorine or bromine atom.

More specifically preferred is a compound of the formula I, in which $R^1$ stands for hydrogen, and $R^2$ and $R^3$ together stand for the 3,4-methylenedioxy group.

The present invention further relates to a process for the manufacture of the compounds of formula I, which comprises heating an acetoacetic acid anilide of the formula II

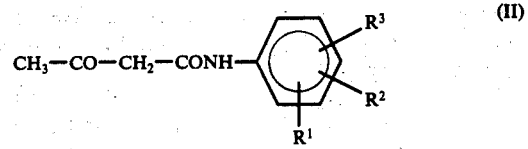

in which $R^1$, $R^2$ and $R^3$ have the meaning given above, with an advantageously at least equimolar amount of an orthoformic acid ester of the formula III

$$HC(OR)_3 \quad (III)$$

in which R stands for an alkyl group of 1 to 4 carbon atoms, preferably methyl or ethyl, and advantageously in a 2-to-4-fold molar excess amount of an acid anhydride, advantageously an aliphatic acid anhydride having 4 to 6 carbon atoms, preferably acetic anhydride, for 30 minutes to 3 hours to a temperature of from 80° to 150° C, preferably to the boiling temperature of the reaction mixture, isolating the resulting 2-alkoxymethylene-acetoacetic acid anilide of the formula IV

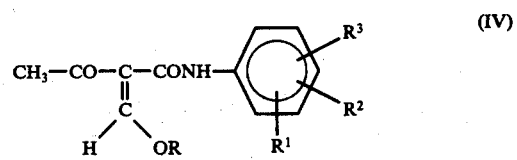

in which R, $R^1$, $R^2$ and $R^3$ have the meaning given above, treating the isolated compound with an advantageously at least equimolar amount of hydroxylamine in an organic solvent or mixture of solvents, preferably methanol, ethanol, propanol, or isopropanol, optionally with the addition of up to 2 parts by volume, preferably up to 1 part by volume, of water per 1 part by volume of organic solvent, at a temperature of from 0° to 100° C, preferably from 10° to 50° C, and treating the resulting isoxazole of the formula V

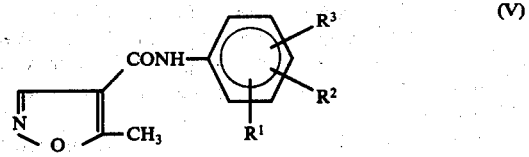

in which $R^1$, $R^2$ and $R^3$ are defined as above, at a temperature of from $-10°$ to $+100°$ C, preferably from $+10°$ to $+50°$ C, with a base, such as sodium hydroxide, potassium hydroxide, sodium carbonate, potassium carbonate, ammonia or an alkali metal alcoholate having 1 to 3 carbon atoms in the alkyl moiety, preferably sodium methylate or ethylate, in an organic solvent, preferably in an alcohol having 1 to 3 carbon atoms, or in a ketone having 3 to 5 carbon atoms, optionally with the addition of water, or with one of the said bases in water without the addition of an organic solvent, and optionally reacting the resulting alkali metal or ammonium compounds of formula I, advantageously with at least the equimolar amount of each of such an acid.

For the above-discussed preparation of the alkali metal or ammonium compounds of formula I, said bases are advantageously used in equimolar amounts or also in a slight excess, especially in a 1.1 to 1.3-molar excess.

The 2-alkoxymethylene-acetoacetic acid anilides of formula IV required as starting material for the manufacture of the compounds of formula I of this invention are new compounds.

Merely the preparation of the 2-ethoxymethylene-acetoacetic acid anilide, which is outside the scope of this invention, from acetoacetic acid anilide, orthoformic acid triethyl ester and acetic anhydride has been described by G. Kempter, W. Schmidt and H. Dost, Chem. Ber. 98, 955 to 961 (1965).

The new 2-ethoxymethylene-acetoacetic acid anilides are compiled in Table 1.

The isoxazoles of formula V are also new compounds, only three analogues of the isoxazoles, in which $R^1$, $R^2$ and $R^3$ each stands for hydrogen, or $R^1$ and $R^2$ each stands for hydrogen and $R^3$ for 2—$CH_3$ or 4—$CH_3$, have been described by F. B. Dains and E. L. Griffin, J. Am. Chem. Soc. 35, 959 to 976 (1913).

The reaction step converting a compound of formula IV to a compound of formula V is surprising. It comprises cyclization of an easily obtainable 2-ethoxymethylene-acetoacetic acid anilide with hydroxyamine to provide an isoxazole of formula V at room temperature with a yield of from 90 to 100%.

The synthesized isoxazoles are compiled in Table 2.

The above-specified ring opening reaction of the isoxazoles of formula V to yield the 2-hydroxy-ethylidene cyano acetic acid anilides of formula I, using bases, is almost quantitative.

The new end products are compiled in Table 3.

The new compounds of formula I exhibit strong anti-inflammatory and analgesic properties. Their anti-inflammatory and analgesic effect is superior to that of phenylbutazone.

When administered in therapeutically usual dosage units, the compounds of the invention show no ulcerogenic effect.

Their anti-inflammatory effect was demonstrated on adjuvant arthritis in rats (Pearson, C. M. and Wood, F. D., Arthrit. Rheumat. 2 (1959), 440); the analgesic effect was demonstrated by means of the writhing test on mice (Sigmund, E. et al., Proc. Soc. Exp. Biol. Med., 95 (1957), 729).

The $ED_{50}$ levels were determined graphically on probability paper. In the writhing test, the $ED_{50}$ is defined to be the dosis of active ingredient that reduces the number of writhings by 50% as compared with a control group. In the adjuvant arthritis test, the effect was judged by observing the inhibition in the secondary lesions, which the animals inflicted to their ears, paws and tails, on the 17th day after the administration of the active substance compositions had started, in comparison with a control group. $ED_{50}$ is considered the dosis that reduces these lesions by 50% as compared to those of the control group.

To examine the ulcerogenic activity, the substances to be tested were orally administered to male rats of a Sprague-Dawley strain, that had been kept unfed for 18 hours, and 24 hours after administration, the gastrointestinal tract of the animals was inspected for ulcers.

In a test for the acute toxicity according to Litchfield and Wilcoxon (Litchfield, J. T. and Wilcoxon, F. W., J. Pharmacol. exp. Ther. 96 (1949), 99), the $LD_{50}$ levels were determined in male or female N.M.R.I. mice or in female Wistar-Lewis rats.

The data found for some compounds of formula I and for the known phenylbutazone are listed in the following Table 4.

TABLE 4

| Substance No. from Table 3 | $ED_{50}$ in mg/kg per os | | $LD_{50}$ in mg/kg per os [1] | | Limit dose in mg/kg per os without ulcerogenic activity |
|---|---|---|---|---|---|
| | writhing | adjuvant arthritis | mice | rats | |
| 2 | ca. 25 | 22 | 585 (492 – 696) | 445 (380 – 521) | 200 |
| 11 | 25 | 28 | 660 (554 – 1117) | 670 [2] (517 – 863) | 100 |
| Phenyl-butazone | 60 – 100 | 37 | 1145 (939 – 1397) | 780 (675 – 901) | 63 |

[1] Limits of confidence for p = 0.05 in brackets
Observation time 7 days
[2] Sprague-Dawley rats used as test animals The following Examples illustrate the invention.

EXAMPLE 1 a. 2-Ethoxymethylene-acetoacetic acid-3,4-dichloro-anilide of formula IV 1.0 Mol of acetoacetic acid-3,4-dichloro-anilide of formula II (246 g) is refluxed for 1.5 hours with 1.12 mols of orthoformic acid triethyl ester of formula III (166 g) and 2.97 mols of acetic anhydride (302 g). After cooling to room temperature, the precipitated crystals are suction-filtered and washed in a mixture of 1 part by volume of benzene and 2 parts by volume of gasoline.

The yield is 251 g, corresponding to 83% of the theoretical yield of 2-ethoxymethylene-acetoacetic acid-3,4-dichloro-anilide.

Melting point after recrystallization from benzene: 125° to 126° C.

| $C_{13}H_{13}Cl_2NO_3$ | molecular weight 302.15 | | |
|---|---|---|---|
| Calculated: | C 51.7 %; | H 4.3 %; | N 4.6% |
| Found: | C 51.8 %; | H 4.1 %; | N 4.5 % |

In a manner analogous to this method, the compounds listed in Table 1 were prepared.

In the case of readily soluble 2-ethoxymethylene-acetoacetic acid anilides, the reaction mixture must under certain circumstances be concentrated by distillation.

b. 5-Methyl-isoxazole-4-carboxylic acid-3,4-dichloro-anilide of formula V 0.11 Mol (7.65 g) of hydroxylamine hydrochloride was dissolved in 30 ml of water, an ice-cold solution of 0.11 mol of sodium hydroxide (4.4 g) in 20 ml of water was added, and the mixture was diluted with 150 ml of methanol. Then, 0.1 mol (30.2 g) of the 2-ethoxymethylene-acetoacetic acid-3,4-dichloro-anilide obtained according to (a) was added, and the mixture was stirred for about 4 hours at room temperature. The solution was then cooled to +5° C, the crystals were suction-filtered and washed with water. After drying in the air, colorless crystals were obtained.

The yield amounted to 26.4 g, corresponding to 97.5% of the theoretical yield of 5-methyl-isoxazole-4-carboxylic acid-3,4-dichloro-anilide. Melting point after recrystallization from methanol: 146° C.

| $C_{11}H_8Cl_2N_2O_2$ | molecular weight: 271.1 | | |
|---|---|---|---|
| Calculated: | C 48.7 %; | H 3.0 %; | N 10.3 % |
| Found: | C 48.6 %; | H 3.0 %; | N 10.2 % |

In an analogous manner, the compounds listed in Table 2 were prepared.

c. 2-Hydroxyethylidene-cyano acetic acid-3,4-dichloro-anilide of formula I

A solution of 0.11 mol (4.4 g) of sodium hydroxide solution in 100 ml of water was added at +10° C to 0.2 mol (27.1 g) of the 5-methylisoxazole-4-carboxylic acid-3,4-dichloro-anilide obtained according to (b) in 100 ml of methanol, the mixture was stirred for 30 minutes and, after dilution with water, the solution was acidified by means of concentrated hydrochloric acid. The precipitated crystal mass was suction-filtered, washed with water and dried in the air. The yield amounted to 26.0 g, corresponding to 96% of the theoretical yield of 2-hydroxyethylidene-cyano acetic acid-3,4-dichloro-anilide.

Melting point (from methanol): 209° to 210° C

| $C_{11}H_8Cl_2N_2O_2$ | molecular weight: 271 | | |
|---|---|---|---|
| Calculated: | C 48.7 %; | H 2.9 %; | N 10.3 % |
| Found: | C 48.9 %; | H 2.7 %; | N 10.4 % |

EXAMPLE 2

2-Hydroxyethylidene-cyano acetic acid-3-trifluoromethylanilide of formula I

A solution of 0.11 mol (4.4 g) of sodium hydroxide solution in 100 ml water was added at +10° C to 0.1 mol (27.0 g) of 5-methyl-isoxazole-4-carboxylic acid-3-trifluoromethyl-anilide of formula V in 100 ml of methanol, the mixture was stirred for 30 minutes and after dilution with water, the solution was acidified by means of concentrated hydrochloric acid. The precipitated crystal mass was suction-filtered, washed with water and dried in the air.

The yield amounted to 26.2 g, corresponding to 97% of the theoretical yield of 2-hydroxy-ethylidene-cyano acetic acid-3-trifluoromethyl-anilide.

Melting point (recrystallization from methanol): 181° to 182° C.

| $C_{12}H_9F_3N_2O_2$ | molecular weight: 270.2 | | |
|---|---|---|---|
| Calculated: | C 53.4 %; | H 3.4 %; | N 10.2 % |
| Found: | C 53.3 %; | H 3.2 %; | N 10.1 % |

In an analogous manner, the compounds listed in Table 3 were prepared.

TABLE 1

Intermediate products of formula IV

| No. | $R_1$ | $R_2$ | $R_3$ | melting point (° C) |
|---|---|---|---|---|
| 1 | H | H | 2-Cl | 95–96 |
| 2 | H | H | 3-Cl | 98 |
| 3 | H | H | 4-Cl | 139.5 |
| 4 | H | 2-Cl | 4-Cl | 127 |
| 5 | H | 2-Cl | 5-Cl | 146 |
| 6 | H | 3-Cl | 4-Cl | 125–126 |
| 7 | H | 3-Cl | 5-Cl | 131 |

TABLE 1-continued

Intermediate products of formula IV

| No. | $R_1$ | $R_2$ | $R_3$ | melting point (° C) |
|---|---|---|---|---|
| 8 | H | H | 3-Br | 118 |
| 9 | H | H | 4-Br | 124 |
| 10 | H | H | 4-F | 127 |
| 11 | H | H | 3-$CF_3$ | 84 |
| 12 | H | 3-$CF_3$ | 5-$CF_3$ | 111 |
| 13 | H | H | 4-$NO_2$ | 160–162 |
| 14 | H | H | 3-$OCF_2$—$CHF_2$ | 73–74 |
| 15 | H | H | 3-$CH_3$ | 73 |
| 16 | H | 2-$CH_3$ | 4-$CH_3$ | 105 |
| 17 | H | H | 2-$OCH_3$ | 94–95 |
| 18 | H | H | 3-$OCH_3$ | 88 |
| 19 | H | H | 4-$OCH_3$ | 94 |
| 20 | H | H | 2-$OC_2H_5$ | 110 |
| 21 | H | 3,4-O—$CH_2$—O | | 136–137 |
| 22 | H | H | 4-$COOC_2H_5$ | 137–138 |
| 23 | H | 2,3 —CH=CH—CH=CH— | | 126 |
| 24 | H | 2-$CH_3$ | 3-Cl | 129 |
| 25 | H | 2-$CH_3$ | 4-Cl | 128 |
| 26 | H | 2-$CH_3$ | 5-Cl | 141 |
| 27 | H | 2-$CF_3$ | 4-Cl | 108 |
| 28 | H | H | 4-O—C₆H₄—Cl | 78–79 |
| 29 | H | H | 4-O—C₆H₄—Br | 88 |
| 30 | H | H | 2-C₆H₅ | 113–114 |
| 31 | H | H | 3-$OCF_2$—CHClF | 62 |
| 32 | H | H | 3-$SCH_3$ | 92 |
| 33 | H | 2-Br | 5-Br | 140 |
| 34 | H | 3-Cl | 4-$CH_3$ | 120 |
| 35 | H | H | 3-I | 148 |
| 36 | H | H | 3-CN | 106.5 |
| 37 | H | 2-$CH_3$ | 5-Br | 140–141 |
| 38 | H | 3-$CH_3$ | 4-Br | 123 |
| 39 | H | H | 3-F | 109.5 |
| 40 | H | 2-$CH_3$ | 3-F | 124–125 |
| 41 | H | 3-Cl | 4-F | 110.5–111.5 |
| 42 | H | 3-$CF_3$ | 4-Cl | 115.5 |
| 43 | H | H | 4-$SCH_3$ | 116–118 |

TABLE 2

Intermediate products of formula V

| No. | $R_1$ | $R_2$ | $R_3$ | melting point (° C) |
|---|---|---|---|---|
| 1 | H | H | 2-Cl | 111–112 |
| 2 | H | H | 3-Cl | 106–107 |
| 3 | H | H | 4-Cl | 151 |
| 4 | H | 2-Cl | 4-Cl | 120–121 |
| 5 | H | 2-Cl | 5-Cl | 122 |
| 6 | H | 3-Cl | 4-Cl | 146 |
| 7 | H | 3-Cl | 5-Cl | 182–183 |
| 8 | H | H | 3-Br | 122 |
| 9 | H | H | 4-Br | 162–163 |
| 10 | H | H | 4-F | 117–118 |
| 11 | H | H | 3-$CF_3$ | 119–120 |
| 12 | H | 3-$CF_3$ | 5-$CF_3$ | 176 |
| 13 | H | H | 4-$NO_2$ | 190–191 |
| 14 | H | H | 3-$OCF_2$—$CHF_2$ | <40 |
| 15 | H | H | 3-$CH_3$ | 80–81 |
| 16 | H | 2-$CH_3$ | 4-$CH_3$ | 160–161 |
| 17 | H | H | 2-$OCH_3$ | 81.5 |
| 18 | H | H | 3-$OCH_3$ | 92–93 |
| 19 | H | H | 4-$OCH_3$ | 133–134 |
| 20 | H | H | 2-$OC_2H_5$ | 105–106 |
| 21 | H | 3,4-O—$CH_2$—O | | 125–126 |
| 22 | H | H | 4-$COOC_2H_5$ | 167.5 |

TABLE 2-continued

Intermediate products of formula V

| No. | R₁ | R₂ | R₃ | melting point (° C) |
|---|---|---|---|---|
| 23 | H | | H -C≡ 2,3 CH \| CH -C H | 137–138 |
| 24 | H | 2-CH₃ | 3-Cl | 158–159 |
| 25 | H | 2-CH₃ | 4-Cl | 147–148 |
| 26 | H | 2-CH₃ | 5-Cl | 127–128 |
| 27 | H | 2-CF₃ | 4-Cl | 133–134 |
| 28 | H | H | 2—⟨O⟩ | 116–117 |
| 29 | H | H | 4-O—⟨O⟩—Cl | 137–138 |
| 30 | H | H | 4-O—⟨O⟩—Br | 138 |
| 31 | H | H | 3-OCF₂—CHClF | 73.5–74.5 |
| 32 | H | H | 3-SCH₃ | 71–72 |
| 33 | H | 2-Br | 5-Br | 171–173 |
| 34 | H | 3-Cl | 4-CH₃ | 149–150 |
| 35 | H | H | 3-I | 148–149 |
| 36 | H | H | 3-CN | 199.5–200.5 |
| 37 | H | 2-CH₃ | 5-Br | 138–139 |
| 38 | H | 3-CH₃ | 4-Br | 130–131 |
| 39 | H | H | 3-F | 122 |
| 40 | H | 2-CH₃ | 3-F | 142 |
| 41 | H | 3-Cl | 4-F | 123–124 |
| 42 | H | 3-CF₃ | 4-Cl | 161–161.5 |
| 43 | H | H | 4-SCH₃ | 135.5–136.5 |

TABLE 3

2-Hydroxyethylidene-cyano acetic acid anilides of formula I

| No. | R₁ | R₂ | R₃ | melting point (° C) |
|---|---|---|---|---|
| 1 | H | H | 2-Cl | 93–94 |
| 2 | H | H | 3-Cl | 168–169 |
| 3 | H | H | 4-Cl | 204.5–205.5 |
| 4 | H | 2-Cl | 4-Cl | 141 |
| 5 | H | 2-Cl | 5-Cl | 118 |
| 6 | H | 3-Cl | 4-Cl | 209–210 |
| 7 | H | 3-Cl | 5-Cl | 227 |
| 8 | H | H | 3-Br | 179 |
| 9 | H | H | 4-Br | 208–209 |
| 10 | H | H | 4-F | 170–171 |
| 11 | H | H | 3-CF₃ | 181–182 |
| 12 | H | 3-CF₃ | 5-CF₃ | 192–193 |
| 13 | H | H | 4-NO₂ | 225–226 |
| 14 | H | H | 3-OCF₂—CHF₂ | 150 |
| 15 | H | H | 3-CH₃ | 131 |
| 16 | H | 2-CH₃ | 4-CH₃ | 109–110 |
| 17 | H | H | 2-OCH₃ | 103 |
| 18 | H | H | 3-OCH₃ | 128–129 |
| 19 | H | H | 4-OCH₃ | 151–152 |
| 20 | H | H | 2-OC₂H₅ | 111 |
| 21 | H | 3,4-O CH₂ O | | 166–167 |
| 22 | H | H | 4-COOC₂H₅ | 149 |
| 23 | H | H | -C≡ 2,3 CH \| CH -C H | 114–115 |
| 24 | H | 2-CH₃ | 3-Cl | 164–165 |
| 25 | H | 2-CH₃ | 4-Cl | 163–164 |
| 26 | H | 2-CH₃ | 5-Cl | 127–128 |
| 27 | H | 2-CF₃ | 4-Cl | 133 |
| 28 | H | H | 4-O—⟨O⟩—Cl | 167–168 |
| 29 | H | H | 4-O—⟨O⟩—Br | 172–173 |
| 30 | H | H | 3-O-CF₂—CHClF | 141 |

TABLE 3-continued

2-Hydroxyethylidene-cyano acetic acid anilides of formula I

| No. | R₁ | R₂ | R₃ | melting point (° C) |
|---|---|---|---|---|
| 31 | H | H | 3-SCH₃ | 135–136 |
| 32 | H | 2-Br | 5-Br | 151–152 |
| 33 | H | 3-Cl | 4-CH₃ | 168–169 |
| 34 | H | H | 3-J | 199–200 |
| 35 | H | H | 3-CN | 206–207 |
| 36 | H | H | Sodium salt of No. 11 | >230 |
| 37 | H | H | 2—⟨O⟩ | |
| 38 | H | 2-CH₃ | 5-Br | |
| 39 | H | 3-CH₃ | 4-Br | |
| 40 | H | H | 3-F | 135–136 |
| 41 | H | 2-CH₃ | 3-F | 139–140 |
| 42 | H | 3-Cl | 4-F | 206–207 |
| 43 | H | 3-CF₃ | 4-Cl | 133–133.5 |
| 44 | H | H | 4-SCH₃ | 162–163 |

We claim:

1. A 2-hydroxyethylidene-cyano acetic acid aniline of the formula

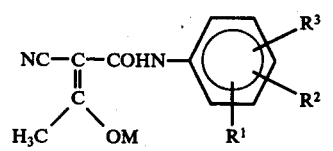

wherein each of R¹, R² and R³, is alkyl of from 1 to 3 carbon atoms, alkoxy of from 1 to 3 carbon atoms, alkylthio of from 1 to 3 carbon atoms; said alkyl, alkoxy or alkylthio substituted in the alkyl moiety by halogen; halogen; nitro; cyano or alkoxycarbonyl of 1 to 3 carbon atoms in the alkyl moiety; also wherein either or both of R¹ and R² are hydrogen, and R³ additionally is phenyl; phenyl substituted by one or two fluorine, chlorine, bromine or iodine atoms, alkyl of from 1 to 3 carbon atoms or alkoxy of from 1 to 3 carbon atoms; phenoxy; or phenoxy substituted by one or two fluorine, chlorine, bromine or iodine atoms, alkyl of from 1 to 3 carbon atoms or alkoxy of from 1 to 3 carbon atoms; but R³ is not methyl when both R¹ and R² are hydrogen; or R¹ is hydrogen, and R² and R³ together are methylenedioxy or, together with the phenyl ring to which they are linked, naphthalene; and M is hydrogen, an alkali metal or ammonium.

2. A compound defined in claim 1, wherein R¹ is hydrogen, and R² and R³ each is halogen or trifluoromethyl.

3. A compound defined in claim 1, wherein R¹ is hydrogen, R² is alkyl of 1 to 2 carbon atoms and R³ is halogen.

4. A compound defined in claim 1, wherein R¹ is hydrogen and R² and R³ together are 3,4-methylenedioxy.

5. A process for the manufacture of a compound as defined in claim 1, which comprises treating an isoxazole of the formula

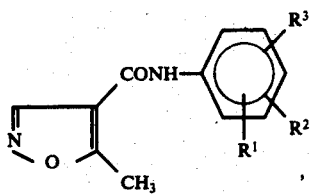

wherein $R^1$, $R^2$ and $R^3$ have the meaning assigned in claim 1, with a base and optionally reacting the resulting alkali metal or ammonium compound as defined in claim 1 with a mineral acid or a strong organic acid.

6. The process defined in claim 5, wherein said isoxazole is treated with the base at a temperature of from $-10°$ to $+100°$ C.

7. A pharmaceutical composition consisting essentially of an effective amount of a compound as defined in claim 1 in admixture or conjunction with a pharmaceutically acceptable carrier and/or constituent.

8. A method of combatting pains and/or inflammations which comprises administering to a patient an effective amount of a compound as defined in claim 1.

* * * * *